US009339026B2

(12) United States Patent
Niazi

(10) Patent No.: US 9,339,026 B2
(45) Date of Patent: May 17, 2016

(54) PNEUMATICALLY AGITATED AND AERATED SINGLE-USE BIOREACTOR

(75) Inventor: Sarfaraz K. Niazi, Deerfield, IL (US)

(73) Assignee: Therapeutic Proteins International, LLC, Chicago, IL (US)

(*) Notice: Subject to any disclaimer, the term of this patent is extended or adjusted under 35 U.S.C. 154(b) by 250 days.

(21) Appl. No.: 13/523,646

(22) Filed: Jun. 14, 2012

(65) Prior Publication Data

US 2012/0252108 A1    Oct. 4, 2012

(51) Int. Cl.
| | |
|---|---|
| C12M 1/02 | (2006.01) |
| C12M 1/04 | (2006.01) |
| A01N 1/02 | (2006.01) |
| B01F 7/16 | (2006.01) |
| B01F 15/00 | (2006.01) |
| B01F 3/04 | (2006.01) |
| C12M 1/00 | (2006.01) |

(52) U.S. Cl.
CPC .......... *A01N 1/0263* (2013.01); *B01F 3/04262* (2013.01); *B01F 7/162* (2013.01); *B01F 15/0022* (2013.01); *B01F 15/0085* (2013.01); *B01F 15/00175* (2013.01); *B01F 15/00525* (2013.01); *C12M 23/14* (2013.01); *C12M 23/28* (2013.01); *C12M 27/04* (2013.01)

(58) Field of Classification Search
CPC .......... A01N 1/0263; B01F 3/00; B01F 3/04; B01F 3/04099; B01F 3/04262; B01F 15/00175; B01F 15/0022; B01F 15/0085; B01F 15/00525; C12M 27/04; C12M 23/14; C12M 23/28
USPC ............................................ 435/284.1, 289.1
See application file for complete search history.

(56) References Cited

U.S. PATENT DOCUMENTS

| | | |
|---|---|---|
| 1,119,370 A | 12/1914 | Queal |
| 1,269,189 A | 6/1918 | Kadish |
| 1,505,204 A | 8/1924 | Keirnan |
| 2,793,166 A | 5/1957 | Alden |
| 3,002,895 A | 10/1961 | Freedman |
| 3,647,397 A | 3/1972 | Coleman |
| 3,677,528 A | 7/1972 | Martin |
| 3,900,186 A | 8/1975 | Balas |
| 3,962,892 A | 6/1976 | Garlinghouse |
| 4,162,855 A | 7/1979 | Bender |

(Continued)

FOREIGN PATENT DOCUMENTS

| | | |
|---|---|---|
| CA | 2271583 | 8/1996 |
| DE | 2017472 | 11/1971 |

(Continued)

OTHER PUBLICATIONS

International Search Report and Written Opinion for PCT/US2012/045627 dated Nov. 22, 2013.

(Continued)

*Primary Examiner* — Michael Hobbs
(74) *Attorney, Agent, or Firm* — Therapeutic Proteins International, LLC; Cheryl Liljestrand; Sarfaraz K. Niazi

(57) ABSTRACT

A single-use round flexible mixing bag for use in bioprocessing in which a fluid is received and agitated using an internal fluid-agitating element comprising a radial flow impeller driven by an internal pneumatic vane motor is disclosed. The bag may include an integral sparger and sensor receiver. Related methods are also disclosed.

11 Claims, 3 Drawing Sheets

(56) References Cited

U.S. PATENT DOCUMENTS

| | | | |
|---|---|---|---|
| 4,209,259 A | 6/1980 | Rains et al. | |
| 4,356,967 A | 11/1982 | Lunick | |
| 4,498,785 A | 2/1985 | de Bruyne | |
| 4,668,632 A | 5/1987 | Young et al. | |
| 4,711,582 A | 12/1987 | Kennedy | |
| 4,783,172 A | 11/1988 | Garg | |
| 4,808,348 A | 2/1989 | Rudick et al. | |
| 4,870,018 A | 9/1989 | Lehmann | |
| 4,978,616 A | 12/1990 | Dean, Jr. et al. | |
| 5,008,197 A | 4/1991 | Wergeland et al. | |
| 5,061,448 A | 10/1991 | Mahe et al. | |
| 5,205,783 A | 4/1993 | Dieckert et al. | |
| RE34,386 E | 9/1993 | Davidson et al. | |
| 5,270,207 A | 12/1993 | Matsumura et al. | |
| 5,401,212 A | 3/1995 | Marvell et al. | |
| 5,501,971 A | 3/1996 | Freedman et al. | |
| 5,591,344 A | 1/1997 | Kenley et al. | |
| 5,656,491 A | 8/1997 | Cassani et al. | |
| 5,727,878 A | 3/1998 | Sullivan, Jr. | |
| 5,750,440 A | 5/1998 | Vanell et al. | |
| 5,779,359 A | 7/1998 | Gambrill et al. | |
| 5,803,137 A | 9/1998 | Shimotoyodome et al. | |
| 5,939,313 A | 8/1999 | Cheng | |
| 5,941,635 A | 8/1999 | Stewart | |
| 5,988,422 A | 11/1999 | Vallot | |
| 6,036,357 A * | 3/2000 | Van Drie | 366/332 |
| 6,071,005 A | 6/2000 | Ekambaram et al. | |
| 6,245,555 B1 | 6/2001 | Curtis | |
| 6,247,840 B1 | 6/2001 | Gaffar | |
| 6,357,907 B1 | 3/2002 | Cleveland et al. | |
| 6,379,625 B1 | 4/2002 | Zuk, Jr. | |
| 6,402,367 B1 | 6/2002 | Lu et al. | |
| 6,439,756 B1 | 8/2002 | Forschner et al. | |
| 6,467,946 B1 | 10/2002 | Gebrian | |
| 6,500,343 B2 | 12/2002 | Siddiqi | |
| 6,514,137 B1 | 2/2003 | Panelli et al. | |
| 6,555,011 B1 | 4/2003 | Tribelsky et al. | |
| 6,637,927 B2 | 10/2003 | Lu et al. | |
| 6,670,171 B2 | 12/2003 | Carll | |
| 6,736,906 B2 | 5/2004 | Cotte et al. | |
| 6,764,859 B1 | 7/2004 | Kreuwel et al. | |
| 6,923,567 B2 | 8/2005 | Bibbo et al. | |
| 7,153,021 B2 | 12/2006 | Goodwin et al. | |
| 7,278,780 B2 | 10/2007 | Goodwin et al. | |
| 7,384,027 B2 | 6/2008 | Terentiev et al. | |
| 7,384,783 B2 | 6/2008 | Kunas et al. | |
| 7,469,884 B2 | 12/2008 | Terentiev et al. | |
| 7,629,167 B2 | 12/2009 | Hodge et al. | |
| 7,762,716 B2 | 7/2010 | Terentiev et al. | |
| 7,992,846 B2 | 8/2011 | Terentiev et al. | |
| 8,123,199 B2 | 2/2012 | Terentiev et al. | |
| 2001/0039369 A1 | 11/2001 | Terentiev | |
| 2002/0082173 A1 | 6/2002 | Terentiev | |
| 2002/0091371 A1 | 7/2002 | Ritter | |
| 2002/0105856 A1 | 8/2002 | Terentiev | |
| 2002/0145940 A1 | 10/2002 | Terentiev | |
| 2003/0008389 A1 | 1/2003 | Carll | |
| 2003/0170810 A1 | 9/2003 | Vedadi et al. | |
| 2003/0226857 A1 | 12/2003 | Bibbo et al. | |
| 2004/0027912 A1* | 2/2004 | Bibbo et al. | 366/149 |
| 2004/0047232 A1 | 3/2004 | Terentiev | |
| 2004/0062140 A1 | 4/2004 | Cadogan et al. | |
| 2004/0218468 A1 | 11/2004 | Terentiev | |
| 2004/0221897 A1 | 11/2004 | Schubmehl et al. | |
| 2004/0229335 A1 | 11/2004 | Zhang et al. | |
| 2004/0252582 A1 | 12/2004 | Bucher | |
| 2005/0002274 A1 | 1/2005 | Terentiev | |
| 2005/0117449 A1 | 6/2005 | Terentiev | |
| 2005/0127215 A1 | 6/2005 | Lienhart et al. | |
| 2005/0163667 A1 | 7/2005 | Krause | |
| 2005/0201201 A1 | 9/2005 | Terentiev | |
| 2005/0239199 A1 | 10/2005 | Kunas et al. | |
| 2005/0272146 A1 | 12/2005 | Hodge et al. | |
| 2006/0092761 A1 | 5/2006 | Terentiev | |
| 2006/0131765 A1 | 6/2006 | Terentiev et al. | |
| 2006/0270036 A1 | 11/2006 | Goodwin et al. | |
| 2007/0030759 A1 | 2/2007 | Terentiev | |
| 2007/0036027 A1* | 2/2007 | Meier | 366/273 |
| 2007/0201993 A1 | 8/2007 | Terentiev et al. | |
| 2007/0220956 A1 | 9/2007 | Terentiev | |
| 2007/0252290 A1 | 11/2007 | Terentiev et al. | |
| 2007/0263484 A1 | 11/2007 | Terentiev | |
| 2008/0008028 A1 | 1/2008 | Terentiev et al. | |
| 2009/0242173 A1 | 10/2009 | Mitchell et al. | |
| 2011/0013474 A1 | 1/2011 | Ludwig et al. | |

FOREIGN PATENT DOCUMENTS

| | | |
|---|---|---|
| DE | 3246330 | 6/1984 |
| DE | 3407370 | 8/1985 |
| DE | 3818776 | 12/1989 |
| DE | 19542227 | 5/1997 |
| DE | 29800818 | 3/1998 |
| DE | 19705118 | 8/1998 |
| DE | 19917398 | 10/2000 |
| DE | 20114076 | 10/2001 |
| EP | 0033292 | 8/1981 |
| EP | 0200792 | 11/1986 |
| EP | 0343885 | 11/1989 |
| EP | 0433463 | 6/1991 |
| EP | 0590473 | 4/1994 |
| EP | 1462155 | 9/2004 |
| FR | 2799138 | 4/2001 |
| GB | 2076677 | 12/1981 |
| GB | 2202549 | 9/1988 |
| JP | 61067476 | 4/1986 |
| JP | 61212275 | 9/1986 |
| JP | 6336825 | 2/1988 |
| JP | 63242297 | 10/1991 |
| JP | 6153902 | 6/1994 |
| JP | 6301626 | 10/1994 |
| JP | 9141079 | 6/1997 |
| JP | 10313718 | 12/1998 |
| JP | 10314569 | 12/1998 |
| WO | WO9833538 | 8/1998 |
| WO | WO9852629 | 11/1998 |
| WO | WO0011953 | 3/2000 |
| WO | WO03028869 | 4/2003 |
| WO | WO2005/037658 | 4/2005 |
| WO | WO2005068059 | 7/2005 |
| WO | WO2005/118771 | 12/2005 |
| WO | WO2006/002091 | 1/2006 |
| WO | WO2006/063087 | 6/2006 |
| WO | WO2007/039600 | 4/2007 |
| WO | WO2008/040567 | 4/2008 |
| WO | WO2008/040568 | 4/2008 |

OTHER PUBLICATIONS

U.S. Appl. No. 60/535,031, filed Jan. 9, 2004, Terentiev.
U.S. Appl. No. 60/599,960, filed Aug. 9, 2004, Terentiev.

* cited by examiner

PNEUMATICALLY AGITATED AND AERATED SINGLE-USE BIOREACTOR

TECHNICAL FIELD

The present invention relates generally to vessels in which fluids are agitated and, more particularly, to a bioreactor.

BACKGROUND OF THE INVENTION

Most pharmaceutical solutions and suspensions manufactured on an industrial scale require highly controlled, thorough mixing to achieve a satisfactory yield and ensure a uniform distribution of ingredients in the final product. Agitator tanks are frequently used to complete the mixing process, but a better degree of mixing is normally achieved by using a mechanical stirrer or impeller (e.g., a set of mixing blades attached to a metal rod). Typically, the mechanical stirrer or impeller is simply lowered into the fluid through an opening in the top of the vessel and rotated by an external motor to create the desired mixing action.

One significant limitation or shortcoming of such an arrangement is the danger of contamination or leakage during mixing. The rod carrying the mixing blades or impeller is typically introduced into the vessel through a dynamic seal or bearing. This opening provides an opportunity for bacteria or other contaminants to enter, which of course can lead to the degradation of the product. A corresponding danger of environmental contamination exists in applications involving hazardous or toxic fluids, or suspensions of pathogenic organisms, since dynamic seals or bearings are prone to leakage. Cleanup and sterilization are also made difficult by the dynamic bearings or seals, since these structures typically include folds and crevices that are difficult to reach. Since these problems are faced by all manufacturers of sterile solutions, pharmaceuticals, or the like, the U.S. Food and Drug Administration (FDA) has consequently promulgated strict processing requirements for such fluids, and especially those slated for intravenous use.

In an effort to overcome these problems, the recent trend in the biotechnology industry is to use disposable plastic bags for a number of bioprocessing steps. Pre-sterilized disposable plastic bags eliminate the need for cleaning, sterilization and validation of the containers after each bioprocessing batch. Their use thus results in substantial saving in the cost of manufacturing of biopharmaceuticals.

Typically, one of the bioprocessing steps used in such manufacturing is growing cell culture(s) in the container, sometimes called a "bioreactor." A traditional bioreactor is a sterile vessel made out of stainless steel or glass with highly controlled environmental parameters including temperature, pH, oxygen concentration, carbon dioxide concentration, which are monitored by permanent sensors built into the rigid vessel. During the cell growth process, the fluid in the bioreactor must also be agitated in order to maintain uniform distribution of temperature, gases and nutrients. As noted above, an impeller typically provides agitation with the blades housed on the shaft connected to an external motor and introduced inside the bioreactor through the dynamic seal in an effort to maintain sterility.

For normal cell growth certain concentration of dissolved oxygen must be maintained. Also, controlled introduction of other gases like carbon dioxide and nitrogen are normally necessary during bioreactor runs. The most efficient way of introducing gases in to bioreactor fluid is sparging, which involves forming small bubbles in the fluid. Such bubbles have large surface to volume ratio and thus can be dissolved more quickly than large size bubbles and thus provide a large kLA value (transport across liquid air interface).

Traditionally, porous solid materials (like titanium) associated with the rigid bioreactor provide sparging. Alternatively, metal sparging rings with small pre-drilled holes are permanently affixed in some rigid bioreactors. In both cases, the bioreactors are not readily disposable and thus must be cleaned and sterilized before reuse for bioprocessing.

In traditional rigid vessel bioreactor, the impeller, sparger, gas, temperature and pH sensors are reusable components that must be cleaned and sterilized after each batch. In the case of disposable bag bioreactors, it is desirable that all the fluid touching components are only used once. This presents the challenging task of providing inexpensive fluid-touching components that can be discarded along with the bag after use.

Another challenge is positioning the components of the bioreactor on the flexible bag. Unlike a rigid vessel, a bioreactor plastic bag (which is basically thin film) has no shape or structural rigidity. Traditionally, bioreactor components like impeller shafts, spargers, sensors are housed on the rigid walls of the vessel by means of threads, bolts or clamps. Obviously, this method of component attachment does not work for plastic bags. To overcome this, many manufacturers offer such solutions as levitating mixing devices, rocking and shaking of bags or compressing the bag externally to produce a wave motion inside the bag. While all of these methods provide some solutions to the problem, many problems in the mixing and aeration remain.

Thus, a need is identified for an improved manner of providing a mixing bag or flexible vessel with an integrated sparger and sensor(s). The improvement provided by the invention would be easy to implement using existing manufacturing techniques and without significant additional expense. Overall, a substantial gain in efficiency and ease of use would be realized as a result of the improvement, and would greatly expand the potential applications for which advanced mixing systems may be used, including bioprocessing.

BRIEF SUMMARY OF THE INVENTION

A disposable bioprocessing apparatus intended for receiving a fluid in need of agitation and sparging using a gas is provided. The apparatus according to one aspect of the disclosure comprises a bag having an upper and a lower flexible wall forming an interior compartment capable of receiving and holding the fluid; a sparger positioned in the interior compartment for forming bubbles from the gas supplied to the fluid when present in the interior compartment; and a fluid-agitating element positioned at the inside bottom of the bag for agitating the fluid radially to assure optimal mixing and assisting in distributing the bubbles throughout the fluid when present in the interior compartment, wherein a rigid base connected to the bag for supporting the fluid-agitating is present. The radial fluid-agitating element is driven by a disposable pneumatic vane motor to prevent any contact from any component from the outside of the bag, a critical step in preventing contamination of the components of the bag. In one embodiment, the bag is of round shape to prevent dead spots of mixing.

DETAILED DESCRIPTION OF THE INVENTION

Figure 1:
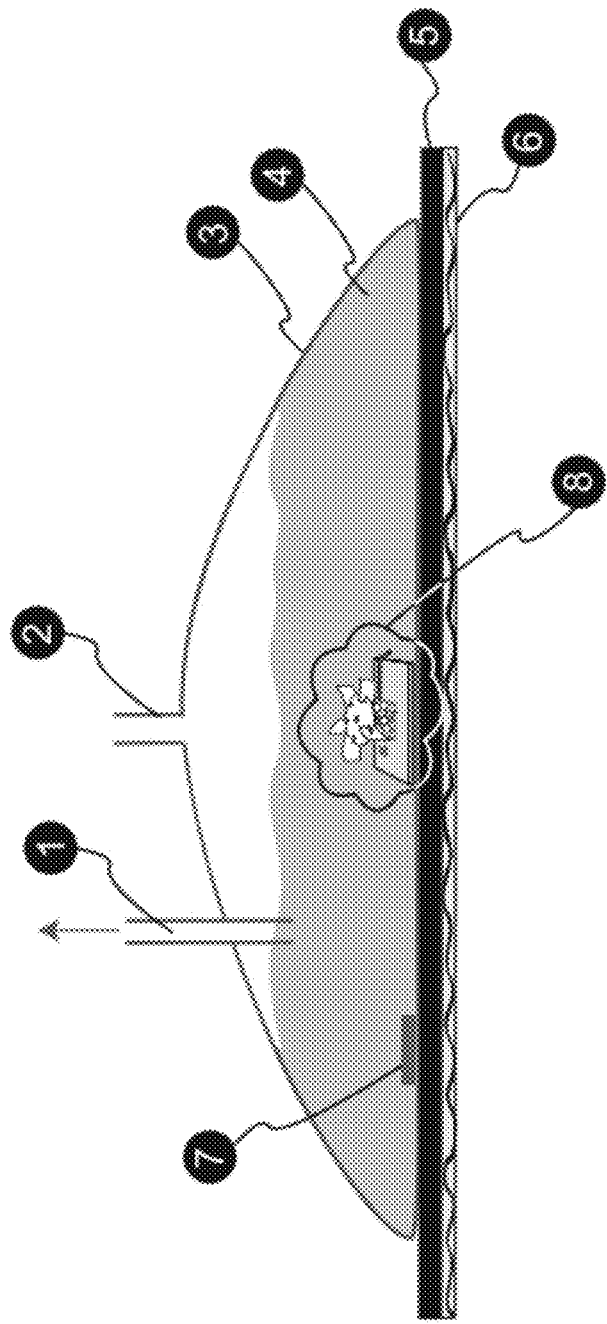
FIG. 1 is a side view of the bioreactor.

Reference is now made to FIG. 1, which discloses one embodiment of the vessel of the present invention in the form of a bag 3, which is flexible and of a round shape. The bag 3 may be hermetically sealed and may have one or more openings or fittings 1 for introducing or recovering a fluid or exhausting a gas 2 or introducing gas (not shown here). Alternatively, the bag 3 may be unsealed or open-ended. The particular geometry of the bag 3 employed is a round shape and is considered critical to the invention. Since the bag 3 is provided with an agitation system 8 that propels the liquid radially from the center to the periphery, having a round shape is required to eliminate any dead spots or unstirred pockets in the bag 3. For specific applications, in the case of a sterile fluid, a hermetically sealed, pre-sterilized bag with an aseptic fitting might be desirable; whereas, in the case where sterility is not important, an open-ended or unsealed bag might be suitable. The main important point is that the bag 3 is capable of receiving and at least temporarily holding a fluid (which is used herein to denote any substance capable of flowing, as may include liquids, liquid suspensions, gases, gaseous suspensions, or the like, without limitation). FIG. 1 further shows the bag 3 containing a fluid 4, a support system for the bag 3 and a heating or cooling element 6 and at least one sensor 7 to monitor the characteristics of the fluid 4.

The flexible the bag 3 may be made from one or more sheets of thin (e.g., having a thickness of between 0.1 and 0.2 millimeters) polyethylene film secured together to define a compartment for receiving the fluid. Preferably, the film used is clear or translucent, although the use of opaque or colored films is also possible.

Figure 2:
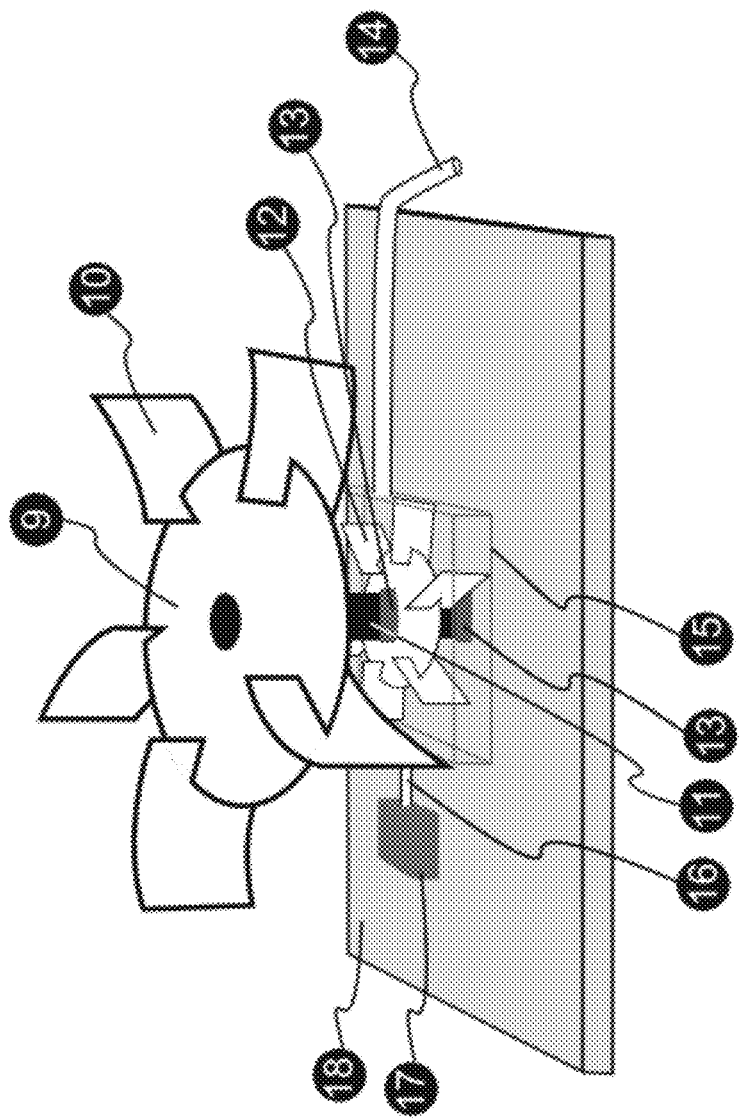
FIG. 2 is a detailed view of the top view of the bag.

The fluid inside the bag 3 is agitated by a fluid-agitating element 8, which is detailed in FIG. 2. In the embodiment of FIG. 2, the fluid-agitating element 8 comprises a radial impeller 10 affixed to a rotating surface 9. The fluid is discharged radially outward to the vessel wall. Compared to axial flow impellers, radial flow impellers provide higher shear and turbulence levels. Radial flow draws the media from the top and bottom and can be used at high speed. The most common impeller styles are the straight or vertical blade and crossed or curved (forward or backward) blade. Any of these types can be used, however, the curved blade provides the best mode of practice as it reduces the stress on the fluid. The fluid-agitating element 8 is also depicted as including a plurality of blades to improve the degree of fluid agitation. The particular number, type, and form of the vanes or blades are not considered important, as long as the desired degree of fluid agitation laterally towards the edges of the bag 3 is provided.

As explained above, it may be desirable to fix the general location or position of the fluid-agitating element 8 within the bag 3; the size or the diameter of the fluid-agitating element is not important but conceivably it is of such size that the movement of liquid reaches to the edge of the bag using reasonable frequency of rotation that will not cause damage to the fluid content. In most instances, the diameter of the blade of fluid-agitating element 8 will be about 10-20% of the diameter of the bag 3 to obtain the maximum benefit of mixing. In accordance with a second aspect of the invention, the fluid-agitating element 8 is located in the center of the bag 3 and attached to the inside face of the lower layer of the bag 3 through a rigid plate 18 to keep the fluid-agitation element 8 from wobbling in the bag 3.

The fluid-agitating element 8 is rotated using a pneumatically driven motor 15 as described in FIG. 2. In pneumatic motors, the pressure of compressed gas is converted to mechanical energy and comprises a working chamber and a set of vanes 12. When the compressed gas from the inlet 14 enters into the working chamber, the vanes are rotated resulting in the movement of the motor shaft 11. Vane air motor speed from 0 to 25,000 rev/min, working pressure of 0.4~0.8 MPa, and the power of 0.6 to 18 kW is readily achieved. Stepless speed changing the input flow can be realized. A pneumatic motor can be used in the presence of fluid. It is noteworthy that the pneumatic motor has a upper bearing 13 surrounding the shaft to allow swift movement at a high speed; these bearings can be traditional ball bearings or non-ball type bearings or sleeves of sufficient rigidity to withstand the repetitive motion of the shaft; at the bottom of the pneumatic motor, the shaft is connected to another lower bearing 13 to allow the shaft 11 to seat properly and allow swift movement.

Turning now to FIG. 2, and as noted in the foregoing description, it may also be desirable to provide the bag 3 with an integral sparger 17 including means for forming bubbles in the fluid. In the illustrated embodiment, the sparger 17 includes a porous surface attached to the exhaust 16 of the pneumatic motor having a porosity ranging from 1 micron to 100 microns. Additionally, porous surface can be provided before the entry point of gas in the pneumatic motor, where the sparging from one source of the sparger is not sufficient, a situation that is more likely to arise when fermenting bacteria. The sparging surface can be made from stainless steel, perforated plastic, a membrane or aluminum oxide or any other hard or soft surface capable diffusing gas out as fine bubbles. In this capacity, the source of energy utilized to turn the pneumatic motor is also utilized to provide aeration of the fluid, making the salient features of the instant invention most energy optimized. The fluid-agitating element 8 is affixed to a hard surface 18, which in turn is attached to the interior surface of the bottom sheet of the bag 3. This allows the fluid-agitating element 8 to stay upright during operation.

Once use of the bag 3 is complete, it may then simply be discarded along with the sparger 10 and fluid-agitation device 8 and the pneumatic motor 6.

Besides a sparger 17 and/or a pneumatic fluid-agitating element 8, it may also be desirable to provide disposable means in the bag 3 to facilitate sensing characteristics of the fluid, such as the pH, oxygen content, temperature, etc. Preferably these sensors 7 (FIG. 1) are of disposable type and embedded in the bag 3 and remote receivers monitor the response to the sensors.

Figure 3:
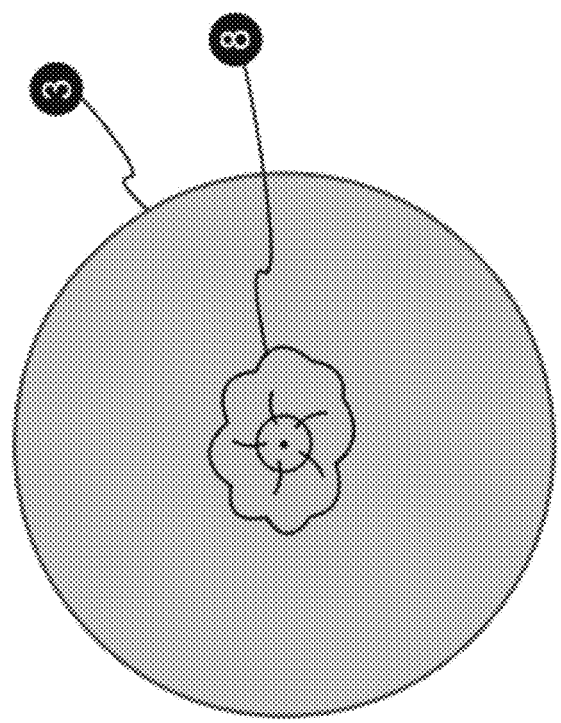
FIG. 3 is a top view of the bioreactor.

FIG. 3 shows a topical view of the bioreactor wherein the round shape of the bag 3 and the location of the fluid agitating element 8 is described.

The foregoing descriptions of various embodiments of the present inventions have been presented for purposes of illustration and description. These descriptions are not intended to be exhaustive or to limit the invention to the precise forms disclosed. The embodiments described provide the best illustration of the principles of the invention and its practical applications to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. A disposable bioprocessing apparatus intended for receiving a fluid in need of agitation and sparging using a gas, comprising:

a round, flexible bag having a round upper sheet with an interior and an exterior surface and an edge and a round lower sheet with an interior and an exterior surface and an edge and wherein the edge of the upper sheet and the edge of the lower sheet are sealed together to form a cavity capable of receiving and holding the fluid;

a gas-driven fluid agitating element for agitating the fluid and assisting in distributing the bubbles comprising a pneumatic motor with a gas inlet and a gas outlet, a shaft and at least one rotating blade attached to the shaft, wherein said gas-driven fluid agitating element is located inside the flexible bag;

a hard support surface affixed at the center of the interior surface of the lower sheet of the bag and to which the gas-driven fluid agitating element is fixed;

a source of compressed gas fluidly connected to the gas inlet of the pneumatic motor, the source of compressed gas supplying compressed gas to the pneumatic motor to drive the at least one rotating blade to agitate the fluid;

a sparger fluidly connected to the gas outlet of the pneumatic motor for forming bubbles, the sparger receiving exhaust gas from the pneumatic motor and aerating the fluid in the bag with the exhaust gas;

a source of compressed gas to operate the pneumatic motor;

a support surface to hold the bag;

at least one liquid port; and at least one gas port.

2. The apparatus according to claim 1, further including a sensor for sensing a condition of the fluid in the bag.

3. The apparatus according to claim 1, further including a means of heating or cooling the fluid in the bag.

4. The apparatus according to claim 1, wherein the rotating blade moves the fluid in a radial direction.

5. The apparatus according to claim 1, wherein the pneumatic motor contains vanes rotated by the flow of gas.

6. A disposable bioprocessing apparatus comprising:
(a) a round, flexible bag comprising a nutrient medium comprising a recombinant organism;
(b) a gas-driven fluid-agitating element for agitating fluid located inside the flexible bag and assisting in distributing bubbles comprising a pneumatic motor with a gas inlet and a gas outlet, a shaft and at least one rotating blade attached to the shaft;
(c) a hard support surface affixed at the center of the interior surface of the lower sheet of the bag and to which the gas-driven fluid agitating element is fixed;
(d) a source of compressed gas fluidly connected to the gas inlet of the pneumatic motor, the source of compressed gas supplying compressed gas to the pneumatic motor to drive the at least one rotating blade to agitate the fluid;
(e) a sparger fluidly connected to the gas outlet of the pneumatic motor for forming bubbles, the sparger receiving exhaust gas from the pneumatic motor and aerating the fluid in the bag with the exhaust gas;
(f) at least one liquid port; and
(g) at least one gas port.

7. The apparatus according to claim 6, wherein the recombinant organism is a bacterium, an animal cell, a plant cell, a virus, or a yeast cell.

8. The apparatus according to claim 6, wherein the recombinant organism is capable of expressing a recombinant protein or antibody.

9. A disposable bioprocessing apparatus comprising:
(a) a round, flexible bag containing a buffer;
(b) a gas-driven fluid-agitating element for agitating fluid located inside the flexible bag and assisting in distributing bubbles comprising a pneumatic motor with a gas inlet and a gas outlet, a shaft and at least one rotating blade attached to the shaft;
(c) a hard support surface affixed at the center of the interior surface of the lower sheet of the bag and to which the gas-driven fluid agitating element is fixed;
(d) a source of compressed gas fluidly connected to the gas inlet of the pneumatic motor, the source of compressed gas supplying compressed gas to the pneumatic motor to drive the at least one rotating blade to agitate the fluid;
(e) a sparger fluidly connected to the gas outlet of the pneumatic motor for forming bubbles, the sparger receiving exhaust gas from the pneumatic motor and aerating the fluid in the bag with the exhaust gas;
(f) at least one liquid port; and
(g) at least one gas port.

10. A disposable bioprocessing apparatus comprising:
(a) a round, flexible bag containing a dilute solution of proteins in need of refolding;
(b) a gas-driven fluid-agitating element for agitating fluid located inside the flexible bag and assisting in distributing bubbles comprising a pneumatic motor with a gas inlet and a gas outlet, a shaft and at least one rotating blade attached to the shaft;
(c) a hard support surface affixed at the center of the interior surface of the lower sheet of the bag and to which the gas-driven fluid agitating element is fixed;
(d) a source of compressed gas fluidly connected to the gas inlet of the pneumatic motor, the source of compressed gas supplying compressed gas to the pneumatic motor to drive the at least one rotating blade to agitate the fluid;
(e) a sparger fluidly connected to the gas outlet of the pneumatic motor for forming bubbles, the sparger receiving exhaust gas from the pneumatic motor and aerating the fluid in the bag with the exhaust gas;
(f) at least one liquid port; and
(g) at least one gas port.

11. A disposable bioprocessing apparatus comprising:
(a) a round, flexible bag containing a body tissue or organ in need of oxygenation;
(b) a gas-driven fluid-agitating element for agitating fluid located inside the flexible bag and assisting in distributing bubbles comprising a pneumatic motor with a gas inlet and a gas outlet, a shaft and at least one rotating blade attached to the shaft;
(c) a hard support surface affixed at the center of the interior surface of the lower sheet of the bag and to which the gas-driven fluid agitating element is fixed;
(d) a source of compressed gas fluidly connected to the gas inlet of the pneumatic motor, the source of compressed gas supplying compressed gas to the pneumatic motor to drive the at least one rotating blade to agitate the fluid;
(e) a sparger fluidly connected to the gas outlet of the pneumatic motor for forming bubbles, the sparger receiving exhaust gas from the pneumatic motor and aerating the fluid in the bag with the exhaust gas;
(f) at least one liquid port; and
(g) at least one gas port.

\* \* \* \* \*